US012673013B2

(12) United States Patent
Nguyen et al.

(10) Patent No.: US 12,673,013 B2
(45) Date of Patent: Jul. 7, 2026

(54) COSMETIC COMPOSITION

(71) Applicant: SHISEIDO COMPANY, LTD., Tokyo (JP)

(72) Inventors: Lethu Nguyen, East Windsor, NJ (US); Joana Motso Lumour-Mensah, East Windsor, NJ (US)

(73) Assignee: SHISEIDO COMPANY, LTD., Tokyo (JP)

( * ) Notice: Subject to any disclaimer, the term of this patent is extended or adjusted under 35 U.S.C. 154(b) by 889 days.

(21) Appl. No.: 17/775,263

(22) PCT Filed: Jan. 21, 2021

(86) PCT No.: PCT/IB2021/050472

§ 371 (c)(1),
(2) Date: May 6, 2022

(87) PCT Pub. No.: WO2021/148986

PCT Pub. Date: Jul. 29, 2021

(65) Prior Publication Data

US 2022/0409501 A1 Dec. 29, 2022

Related U.S. Application Data

(60) Provisional application No. 62/964,527, filed on Jan. 22, 2020.

(51) Int. Cl.

| | |
|---|---|
| ***A61K 8/25*** | (2006.01) |
| ***A61K 8/06*** | (2006.01) |
| ***A61K 8/894*** | (2006.01) |
| ***A61K 8/92*** | (2006.01) |
| ***A61Q 1/02*** | (2006.01) |

(52) U.S. Cl.

CPC ................ *A61K 8/25* (2013.01); *A61K 8/064* (2013.01); *A61K 8/894* (2013.01); *A61K 8/92* (2013.01); *A61Q 1/02* (2013.01); *A61K 2800/43* (2013.01); *A61K 2800/48* (2013.01)

(58) Field of Classification Search

CPC .......... A61K 8/25; A61K 8/064; A61K 8/894; A61K 8/92; A61K 2800/43; A61K 2800/48; A61K 8/19; A61K 8/375; A61K 8/87; A61K 8/891; A61K 8/895; A61Q 1/02; A61Q 1/12

See application file for complete search history.

(56) References Cited

U.S. PATENT DOCUMENTS 2,676,182 A 4/1954 Herbert et al.
3,627,851 A 12/1971 Brady
3,772,247 A 11/1973 Flannigan
4,877,604 A 10/1989 Schlossman
4,935,484 A 6/1990 Wolfgruber et al.
5,063,254 A 11/1991 Nakos
5,075,103 A 12/1991 Halloran et al.
5,082,706 A 1/1992 Tangney
5,108,736 A 4/1992 Schlossman
5,110,890 A * 5/1992 Butler .................... C08G 77/06 528/30
5,248,739 A 9/1993 Schmidt et al.
5,302,685 A 4/1994 Tsumura et al.
5,319,040 A 6/1994 Wengrovius et al.
6,103,250 A * 8/2000 Brieva ..................... A61K 8/26 514/474
6,153,689 A * 11/2000 Itoh ...................... C09D 183/06 524/588
7,964,178 B2 6/2011 Gutkowski et al.
8,673,327 B2 3/2014 Lemoine et al.
9,328,244 B2 5/2016 O'Halloran et al.
2004/0265348 A1* 12/2004 Hollenberg .............. A61K 8/11 424/401
2007/0071703 A1 3/2007 Lin
2007/0148115 A1* 6/2007 Cook ....................... A61Q 1/02 424/70.12
2008/0081022 A1* 4/2008 Yu ........................... A61Q 1/02 424/78.37
2009/0068238 A1 3/2009 Themens et al.
2009/0185984 A1 7/2009 Gutkowski et al.
2010/0260700 A1 10/2010 Dop
2010/0260701 A1* 10/2010 Dop ......................... A61Q 1/10 424/78.02
2012/0288462 A1* 11/2012 Lebok ................. A61K 8/0229 514/769
2015/0110884 A1 4/2015 Arditty et al.
2018/0028025 A1 2/2018 Farahat et al.
2019/0060188 A1 2/2019 Ranade et al.

(Continued)

FOREIGN PATENT DOCUMENTS

CN 110167514 A 8/2019
JP 2011-513407 A 4/2011
JP 2015-518868 A 7/2015

(Continued)

OTHER PUBLICATIONS

Bin et al. "Composition for Reducing Drying Time of Hair and Improving Softness Thereof" WO2016175524A1—machine translation (Year: 2016).*

WO2017057862A1—machine translation. Han et. al. "Makeup Composition Having Reduced Transfer, and Preparation Method Therefor" 2017 (Year: 2017).*

WO2017057862A1—machine translation + tables; Han et al. "Makeup Composition Having Reduced Transfer, and Preparation Method Therefor" (Year: 2017).*

Global Cosmetic Industry "13 Innovation Takeaways from in-cosmetics North America" (2018) (Year: 2018).*

(Continued)

*Primary Examiner* — Sean M Basquill
*Assistant Examiner* — Rajan Pragani
(74) *Attorney, Agent, or Firm* — Foley & Lardner LLP

(57) ABSTRACT

Provided is a cosmetic composition which includes at least one silicone resin and at least one emulsifier.

12 Claims, No Drawings

(56) References Cited

U.S. PATENT DOCUMENTS

| | | | | |
|---|---|---|---|---|
| 2020/0085701 | A1* | 3/2020 | Debeaud | A61Q 1/06 |
| 2020/0113791 | A1 | 4/2020 | Manet et al. | |

FOREIGN PATENT DOCUMENTS

| | | | | |
|---|---|---|---|---|
| JP | 2020-514262 | A | 5/2020 | |
| WO | WO-2009/071662 | A2 | 6/2009 | |
| WO | WO-2016175524 | A1 * | 11/2016 | A61K 8/34 |
| WO | WO-2017057862 | A1 * | 4/2017 | A61Q 1/00 |
| WO | WO-2018115256 | A1 * | 6/2018 | A61K 8/345 |
| WO | WO-2019/122158 | A1 | 6/2019 | |

OTHER PUBLICATIONS

UL Prospector "Granresin PHQ-Fluid", 2018. (Year: 2018).*

WO2017057862A1—machine translation provided. Han. "Makeup Composition Having Reduced Transfer, and Preparation Method Therefor" 2017 (Year: 2017).*

"NIA 24 Sun Damage Prevention 100% Mineral Sunscreen SPF 30", COSDNA, Mar. 10, 2010, retrieved from https://www.cosdna.com/chs/cosmetic_6bae30227.html.

Maxon et al., "Formulation Possibilities With New Silicone Polyphenylsilsequioxane Liquid Resins for Skin Care, Hair Care and Color Cosmetic Applications", ip.com, ip.com Inc., West Henrietta, NY, US, Jan. 8, 2020, pp. 1-17, XP013185415.

Office Action issued in corresponding Chinese Patent Application No. 202180006847.9 dated Mar. 9, 2024 (10 pages).

Office Action issued in corresponding European Patent Application No. 21701857.1 dated Apr. 3, 2024 (3 pages).

Spencer, Natasha, "Grant Industries Introduces Super Grant Girl Fizz Mask in Korea", Cosmetic Design, Jun. 20, 2018, pp. 1-2.

PCT International Preliminary Report on Patentability issued in corresponding PCT Application No. PCT/IB2021/050472, dated Aug. 4, 2022.

Office Action issued in corresponding Chinese Patent Application No. 202180006847.9 dated Jul. 30, 2024 (7 pages).

International Searching Authority, "International Search Report," issued in connection with International Patent Application No. PCT/IB2021/050472, dated Apr. 22, 2021.

International Searching Authority, "Written Opinion," issued in connection with International Patent Application No. PCT/IB2021/050472, dated Apr. 22, 2021.

Encyclopedia of Polymer Science and Engineering, vol. 15, John Wiley and Sons, New York, 1989, pp. 265-270.

Office Action issued in corresponding Chinese Patent Application No. 202180006847.9 dated Mar. 6, 2025.

Office Action issued in corresponding Japanese Patent Application No. 2022-530821 dated Feb. 4, 2025.

Office Action issued in Japanese Patent Application No. 2022-530821 dated Aug. 5, 2025.

* cited by examiner

COSMETIC COMPOSITION

PRIORITY

The present application claims priority under 37 U.S.C. § 371 to International Patent Application No. PCT/IB2021/050472, filed Jan. 21, 2021, which claims priority to and the benefit of U.S. Provisional Application No. 62/964,527 filed Jan. 22, 2020. The contents of these applications are hereby incorporated by reference in their entireties.

FIELD

The present disclosure relates in general to cosmetic compositions, and specifically to anhydrous cosmetic compositions and compositions containing a low amount of water and their methods of making and methods of use.

SUMMARY

One embodiment is an anhydrous cosmetic composition comprising at least one silicone resin and at least one emulsifier.

Yet another embodiment is a cosmetic composition comprising at least one resin silicone resin; at least one emulsifier; and less than about 10% of water.

DETAILED DESCRIPTION

Unless otherwise specified "a" or "an" means one or more.

As used herein, the term "about" placed before a specific numeric value may mean±20% of the numeric value; ±18% of the numeric value, ±15% of the numeric value; ±12% of the numeric value; ±8% of the numeric value; ±5% of the numeric value; ±3% of the numeric value; ±2% of the numeric value; ±1% of the numeric value or ±0.5% of the numeric value.

Unless otherwise specified, all content information for ingredients of compositions expressed as % refers to % by mass, relative to the total mass of the composition, unless specified otherwise.

Current long wear lip compositions may have a number of deficiencies. For example, they may be very sticky and uncomfortable to wear. They may also contract skin and make lips dry. In addition, if they are liquids, they may spill out of a container holding the composition.

The present inventors developed a cosmetic composition, which may eliminate one or more deficiencies of the current long wear lip compositions. In particular, the present inventors developed a cosmetic composition comprising at least one silicone resin and at least one emulsifier, which may contain a low amount of water and/or be anhydrous. As used herein, the term "anhydrous" may mean that the composition contains less than 5 mass % of water or less than 4.5% of water or less than 4% of water or less than 3.5% of water or less than 3% of water or less than 2.5% of water or less than 2% of water or less than 1.5% of water or less than 1% of water or 0.5 mass % of water or less than 0.2 mass % of water or less than 0.1 mass % of water or less than 0.05 mass % of water or less than 0.02 mass % of water or less than 0.01 mass % of water.

In some embodiments, water that may be present in the composition as, for example, bound water, which may be, for example, water of crystallization in salts, and/or as traces of water absorbed by one or more starting materials (raw materials) used in the preparation of the composition.

In some embodiments, the composition may contain a low amount of water, which may mean that the water content in the composition is about 10% or less. This amount of water may be a part of one or more starting materials (raw materials) and/or may be present as a part of one or more solvents. With this amount, the composition may be processed as, for example, an emulsion. The present composition may have a smooth and creamy texture, which may provide a good coverage using a single application of the composition to a keratinous surface, such as skin, e.g. lips, of a subject, such as a human being. At the same time, the composition may be light/weightless to wear.

The composition may be a long wear composition. As used herein, the term "long wear" means that the composition may be worn for at least 4 hours up 24 hours or for at least 6 hours up to 24 hours or for at least 8 hours up to 24 hours or at least for at least 10 hours up to 24 hours or for at least 12 hours up to 24 hours or for at least 14 hours or for at least 16 hours or for at least 18 hours without interruption of esthetical appearance. The present composition may also have a silky feel with no skin pulling due to the presence of at least one emulsifier, which may contain in some embodiments, at least one silicone emulsifier, at least one polyglyceryl emulsifier or a combination thereof.

The present composition may be creamy in texture, comfortable to wear with a vibrant, lively color. The present composition may provide a long lasting makeup effect and at the same time have refreshing and moisturizing/hydrating properties. The present composition may be highly pigmented and have a good coverage, meaning that the deposit of composition on keratinous surface, such as skin, e.g. lips, is dense and uniform. The present composition may be easy to remove with, for example, an oil based remover. The present composition may not stain which is perceived by consumers as a beneficial characteristic. The present composition may be non-sticky and comfortable to wear. The present composition may be stable without separating over time.

The present composition may be used in a number of color cosmetics products. In addition, applications of the present composition may include skin care products, sun care products, deodorants or hair products. In such products, the composition may be in a form of a liquid, such as a thick liquid, a gel or a cream or in a solid form. In some embodiments, the composition may be a lip composition, such as a lipstick or lip balm composition. In some embodiments, the composition may be a blush composition. In some embodiments, the composition may be a foundation composition. In some embodiments, the composition may be a concealer composition. In some embodiments, the composition may be an eye brow composition. In some embodiments, the composition may be a mascara composition. In some embodiments, the composition may be a sunscreen composition.

Although in some embodiments, the composition may contain high concentrations of texturizing powder(s) and pigment(s), the composition may remain stable and have a great makeup retention.

As used herein, the term "stable" means that the composition does not undergo any of separation of its ingredients, a change in color and/or a change in texture over time, such as up to two years at ambient conditions (e.g., 25° C./65% RH) and four weeks at accelerated conditions (e.g., 50° C./65% RH).

In some embodiments, the cosmetic composition can be used alone. In other words, the composition may be applied alone, without another composition, to a keratinous surface or substrate, such as skin, e.g. lips, or hair, of a subject, such as a human.

In some embodiments, the cosmetic composition may be used together with another product, for example, a top coat, a primer, or a powder.

The composition may comprise at least one silicone resin which may be a solid or a liquid. The term "silicone resin" may mean a multidimensional structure, such as, for example, a branched or a cage-like structure, with a basic backbone polymer structure comprising or made of alternating silicon and oxygen atoms.

Silicone resins, which are also known as siloxane resins, may be described using the "MDTQ" nomenclature, the resin being described as a function of the various siloxane monomer units it comprises, each of the letters "MDTQ" characterizing a type of unit.

The letter "M" represents a mono-functional unit of formula $R_1R_2R_3SiO$, with the silicon atom being bonded to only one oxygen.

The letter "D" represents a di-functional unit $R_1R_2SiO_2$ in which the silicon atom is bonded to two oxygen atoms.

The letter "T" represents a trifunctional unit of formula $R_1SiO_3$, in which the silicon atom is bonded to three oxygen atoms.

The letter "Q" represents a quarto-functional unit of formula $SiO_4$, in which the silicon atom is bonded to four oxygen atoms.

Such resins are described, for example, in the Encyclopedia of Polymer Science and Engineering, vol. 15, John Wiley and Sons, New York, (1989), pp. 265-270, and U.S. Pat. Nos. 2,676,182, 3,627,851, 3,772,247, 5,248,739, 5,082,706, 5,319,040, 5,302,685 and 4,935,484.

In the units M, D and T, It, functional groups, i.e. $R_1$, $R_2$ and $R_3$, may be the same or different. Each of $R_1$, $R_2$ and $R_3$ may be, for example, a hydrocarbon-based radical, such as an alkyl group, containing from 1 to 10 carbon atoms, an aryl group, including a phenyl group, a phenylalkyl group or a hydroxyl group.

Various silicone resins with different properties may be obtained from various combinations of units, the properties of these polymers varying as a function of the type of monomer (or unit), the nature and number of the radical(s) $R_i$, the length of the polymer chain, the degree of branching and the size of the side chains. A silicone resin used in the composition may be, for example, of a silicone resin of MQ type, a silicone resin of T type, a silicone resin of MQT type or a combination thereof. The use of D unit may be optional. However, it may be preferred that a silicone resin, such as an MQT resin, does not contain any D unit(s). In some embodiments, the at least one silicone resin may comprise at least one MQT silicone resin, which may be for example, a phenyl modified MQT silicone resin (MQT-Ph resin). In some embodiments, the at least one silicone resin may comprise polyphenylsilsesquioxane and trimethylsiloxysilicate.

Silicone resins, which may be used in the composition, are disclosed, for example, U.S. Pat. Nos. 5,110,890, 5,075,103, 5,063,254.

The silicone resin may be used, for example, in a solid, powder form or may be solubilized in an organic liquid. In some embodiments, the at least silicone resin may be solubilized in a volatile solvent, such as a hydrocarbon solvent, e.g. isododecane, or a silicone solvent, e.g. dimethicone. A silicone resin composition comprising polyphenylsilsesquioxane/trimethylsiloxysilicate resin solubilized in dimethicone is commercially available from Grant Industries, NJ, USA under the tradename Granresin PHQ [INCI name:-Polyphenylsilsesquioxane/Trimethylsiloxysilicate (and) dimethicone]. Granresin-PHQ contains about 80% of a polyphenylsilsesquioxane/trimethylsiloxysilicate resin (active) in about 20% of dimethicone. Another commercial silicone resin is known as Granresin MQI-T50 (INCI: Isododecane and Polymethylsilsesquioxane/Trimethylsiloxysilicate), also available from Grant Industries.

An amount of the at least one silicone resin in the composition may vary. In some embodiments, the at least one silicone resin may be used in solubilized form (resin solubilized in solvent) and for example, an amount of such at least one silicone resin may be from about 0.01 mass % to about 40.0 mass %, from about 0.1 mass % to about 38.0 mass or from about 0.5 mass % to about 35.0 mass % or from about 1.0 mass % to about 30 mass or from about 2.0 mass % to about 20 mass %.

In some embodiments, the amount of a solid resin (active, not solubilized in solvent) may be from about 0.008 mass % to about 34.0 mass %, from about 0.085 mass % to about 33.0.0 mass % or from about 0.45 mass % to about 30.0 mass % or from about 0.9.0 mass % to about 26.0 mass % or from about 1.7 mass % to about 17.0 mass %.

In some embodiments, the composition contains at least one emulsifier. In some embodiments, the at least one emulsifier is selected from ionic, such as anionic, emulsifiers; nonionic hydrocarbon based emulsifiers, silicone emulsifiers, which may be nonionic, and mixtures thereof.

In some embodiments, the at least one emulsifier may comprise at least one emulsifier with an HLB value of 8 or less. "HLB" refers to the "hydrophilic-lipophilic balance" associated with emulsifiers. HLB value relates to the ratio of hydrophilic groups and lipophilic groups in emulsifiers, and also relates to solubility of the emulsifiers. Typically, lower HLB emulsifiers are more soluble in lipophilic materials or oils and are more appropriate for use in water-in-oil (W/O) emulsions. On the other hand, higher HLB emulsifiers are more soluble in water or hydrophilic materials and are more suitable for oil-in-water (01 W) emulsions.

In some embodiments, the at least one emulsifier may comprise at least one silicone based water-in-oil emulsifier, which may be selected, for example, from alkyldimethicone copolyol emulsifiers and dimethicone copolyol emulsifiers.

In some embodiments, an alkyldimethicone copolyol emulsifier may be an emulsifier having formula (I) below:

(I)

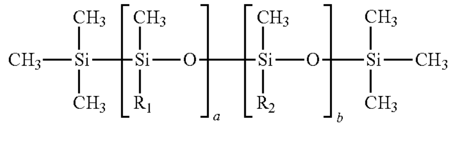

in which:

$R_1$ denotes a linear or branched, $C_{12}$-$C_{20}$, preferably $C_{12}$-$C_{18}$, alkyl group;

$R_2$ denotes the group: $—C_nH_{2n}—(—OC_2H_4—)_x—(—OC_3H_6—)_y—O—R_3$;

$R_3$ denotes a hydrogen atom or a linear or branched alkyl radical containing from 1 to 12 carbon atoms;

a is an integer ranging from 1 to approximately 500;

b denotes an integer ranging from 1 to approximately 500;

n is an integer ranging from 2 to 12, and preferably from 2 to 5;

x denotes an integer ranging from 1 to approximately 50, and preferably from 1 to 30;

y denotes an integer ranging from 0 to approximately 49, and preferably from 0 to 29, with the proviso that, when y is other than zero, the ratio x/y is greater than 1, and preferably ranges from 2 to 11.

In some embodiments, the alkyldimethicone copolyol emulsifiers of formula (I) may be cetyl PEG/PPG-10/1 dimethicone, and more particularly the cetyl PEG/PPG-10/1 dimethicone and dimethicone (INCI name) mixture, such as the product sold under the trade name Abil EM90 by the company Goldschmidt, or else the (polyglyceryl-4-stearate and cetyl PEG/PPG-10 (and) dimethicone (and) hexyl laurate) mixture, such as the product sold under the trade name Abil WE09 by the same company.

In some embodiments, a dimethicone copolyol emulsifier may be an emulsifier having formula (II) below:

(II)

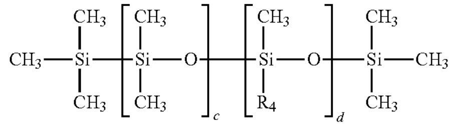

in which:

$R_4$ denotes the group: $-C_mH_{2m}-(-OC_2H_4-)_s-(-OC_3H_6)_t-O-R_5$;

$R_5$ denotes a hydrogen atom or a linear or branched alkyl radical containing from 1 to 12 carbon atoms;

c is an integer ranging from 1 to approximately 500;

d denotes an integer ranging from 1 to approximately 500;

m is an integer ranging from 2 to 12, and preferably from 2 to 5;

s denotes an integer ranging from 1 to approximately 50, and preferably from 1 to 30;

t denotes an integer ranging from 0 to approximately 50, and preferably from 0 to 30; with the proviso that the sum s+t is greater than or equal to 1.

In some embodiments, a dimethicone copolyol emulsifier of formula (II) may be PEG-18/PPG-18 dimethicone.

In some embodiments, the at least one emulsifier may comprise at least one emulsifier of formula (II).

In some embodiments, the at least one emulsifier may comprise a water-in-oil emulsifier having an HLB value less than 8.0, such as from 2.0 to 7.0 or from 3.0 to 6.0 or from about 4.0 to about 5.0, e.g. about 4.5, including any value or subrange within these ranges. In some embodiments, the at least one emulsifier may contain at least one silicone emulsifier, which may include, for example, at least one silicone W/O emulsifier. In some embodiments, the at least one emulsifier may comprise PEG/PPG-18/18 dimethicone. In some embodiments, the at least one emulsifier may further comprise a silicone volatile solvent, either dimethicone or cyclopentasiloxane. An emulsifier comprising PEG/PPG-18/18 dimethicone is commercially available from Grant Industries, NJ, USA under the tradename Gransurf 50C-HM (INCI name: PEG/PPG-18/18 dimethicone (and) dimethicone). Gransurf 50C-HM is a water-in-oil emulsifier with an HLB value of about 4.5. Gransurf 50C-HM contains about 50% of PEG/PPG-18/18 dimethicone (active).

Other useful silicone emulsifiers may include cyclopentasiloxane (and) PEG-18/PPG-18 dimethicone (INCI name) mixture, sold by the company Dow Corning under the trade name Silicone DC 5225 C, or KF-6040 from the company Shin Etsu.

Emulsifiers which may be used in the composition are disclosed, for example, in U.S. Pat. No. 8,673,327, WO2019122158.

An amount of the at least one emulsifier used as solubilized form or as a composition (mixture) of multiple emulsifiers within the composition may vary. For example, it may be from about 0.01 mass % to about 7.0 mass %, from about 0.01 mass % to about 5.0 mass %, from about 0.1 mass % to about 4.0 mass % or from about 0.5 mass % to about 3.5 mass % or from about 0.7 mass % to about 3.0 mass % or from about 0.8 mass % to about 2.0 mass % or from about 2.0 mass % to about 7.0 mass % or from about 3.0 mass % to about 6.0 mass %.

In another embodiment, the amount of active emulsifier (emulsifier without solvent) may from about 0.005 mass % to about 2.5 mass %, from about 0.05 mass % to about 2.0 mass or from about 0.25 mass % to about 1.8 mass % or from about 0.35 mass % to about 1.5 mass or from about 0.4 mass % to about 1.0 mass %.

In some embodiments, the at least one emulsifier may comprise at least one polyglyceryl emulsifier. In some embodiments, the at least one polyglyceryl emulsifier may comprise at least one water-in-oil polyglyceryl emulsifier having an HLB value less than about 8.0, such as from about 3.0 to about 7.0 or from about 3.0 to about 6.0 or from about 4.0 to about 5.0, including any value or subrange within these ranges. In some embodiments, the at least one polyglyceryl emulsifier may comprise at least one oil-in-water polyglyceryl emulsifier having an HLB value greater than about 8.0, such as from about 8.0 to about 14.0 or from about 8.5 to about 13.0 or from about 9.0 to about 12.0, including any value or subrange within these ranges. Yet in some embodiments, the at least one polyglyceryl emulsifier may comprise at least one water-in-oil polyglyceryl emulsifier and at least one oil-in-water polyglyceryl emulsifier.

In some embodiments, at least one polyglyceryl emulsifier may comprise at least one polyglyceryl ester. Examples of polyglyceryl esters may include, but are not limited to, polyglyceryl 2 esters, such as polyglyceryl 2 stearate, polyglyceryl 2 caprate, polyglyceryl 2 oleate, polyglyceryl 2 sesquiolate, polyglyceryl 2 triisostearatem polyglyceryl 2 dipolyhydroxystearate, polyglyceryl 2 isostearate; polyglyceryl 3 esters, such as polyglyceryl 3 diisostearate; polyglyceryl 3 caprate, polyglyceryl 3 oleate, polyglyceryl 3 laurate, polyglyceryl 3 palmitate, polyglyceryl 3 ricinoleate; polyglyceryl 4 esters, such as polyglyceryl 4 oleate, polyglyceryl 4 caprate, polyglyceryl 4 isostearate, polyglyceryl 4 laurate, polyglyceryl 4, cocoate, polyglyceryl 4 dipolyhydroxystearate, polyglyceryl 4 diisostearate; polyglyceryl 6 esters, such as polyglyceryl 6 polyhydroxystearate, polyglyceryl 6 caprylate, polyglyceryl 6 oleate, polyglyceryl 6 polyricinoleate, polyglyceryl 6 distearate, polyglyceryl 6 stearate, polyglyceryl 6 behenate, polyglyceryl 6 laurate; polyglyceryl 10 esters, such as polyglyceryl 10 laurate, polyglyceryl 10 myristate, polyglyceryl 10 caprylate, polyglyceryl 10 oleate, polyglyceryl 10 dioleate, polyglyceryl 10 diisostearate, polyglyceryl 10 pentastearate; polyglyceryl 10. Polyglyceryl esters may have hydrophilic-lipophilic balance (HLB) varying depending on the length of the polyglycerol chain and the degree of esterification. The HLB of polyglyceryl esters vary from 3 to 14, and the desired HLB value may be obtained by appropriate blending. In some embodiments, the at least one polyglycerine emulsifier may comprise at least one water-in-oil polyglyceryl ester emulsifier having an HLB value less than about 8.0, such as from about 3.0 to about 7.0 or from about 3.0 to about 6.0 or from about 4.0 to about 5.0, including any value or subrange within these ranges.

In some embodiments, the composition may comprise at least one polyglyceryl emulsifier comprises at least one of a polyglyceryl-6 ester, such as polyglyceryl-6 polyhydroxystearate and/or polyglyceryl-6 polyricinoleate, and a polyglyceryl-3 ester, such as polyglyceryl-3 diisostearate.

In some embodiments, the composition may comprise one or more specific polyglyceryl ester(s) selected from polyglyceryl-6 polyhydroxystearate, polyglyceryl-6 polyricinoleate, polyglyceryl-6, polyglyceryl-3 diisostearate.

In some embodiments, the composition may comprise each of polyglyceryl-6 polyhydroxystearate, polyglyceryl-6 polyricinoleate, and polyglyceryl-3 diisostearate.

Polyglyceryl esters are commercially available from a number of vendors. For example, Emulium® Illustro, which is a W/O emulsifier containing polyglyceryl-6 polyhydroxystearate and polyglyceryl-6 polyricinoleate, and Plurol® Diisostearique CG is a natural, PEG-free, W/O sensory emulsifier containing polyglyceryl-3 diisostearate, are commercially available from Gattefosse, France.

In some embodiments, the at least one emulsifier may include the following emulsifiers in the following amounts with respect to the total composition: polyglyceryl 6-polyhydroxystearate: about 1.387%; polyglyceryl 6-polyricinoleate: about 1.387%; polyglyceryl 6: about 0.225%.

In some embodiments, the composition may further comprise at least one pigment, which may include at least one treated pigment, at least one untreated pigment, at least one dye, which may be, for example, a water and oil soluble dye, or any combination thereof.

In some embodiments, the at least one treated pigment may include at least one hydrophobically treated pigment.

The term "hydrophobic" typically means that the substance, because of its nonpolar structure, is difficult to dissolve in water. The term "hydrophilic" on another hand means that the substance is dissolvable in water or other polar solvents due to its hydrogen bonding ability.

Hydrophobic treatment for a treated pigment may be at least one treatment selected from treatments with silicones, metal soaps, fatty acids, alkyls and its derivatives, amino acids and their derivatives, natural waxes, polyacrylate, polyethylene, urethane, aluminum laurate, aluminum stearate, chitin, collagen, fluorochemical, lecithin, silane, titanatate ester, perfluoropolymethylisopropyl ether, styrene acrylates copolymer, magnesium myristate, lauroyl lysine and a combination thereof. Treated pigments, such as titanate treated pigments, are commercially available, for example, from Kobo Products, Inc. Treated pigments are disclosed, for example, in U.S. Pat. Nos. 4,877,604, 5,108,736, 7,964,178, 9,328,244; U.S. patent application publications nos. 200918598 and 2018028025. In some embodiments, a treated pigment may include a pigment color additive and a titanate agent, such as titanium dioxide or isopropyl titanium triisostearate. In some embodiments, a treated pigment may further comprise at least additional component such as methicone, dimethicone, aluminum hydroxide, polyhydroxystearic acid, silanes, e.g. triethoxycaprylylsilane, polyurethanes. Examples of pigment color additives include, but not limited to, dyes and lakes, such as Red 30 lake, Red 27 lake, Red 28 lake, Red 33 lake, Red 40 lake, Red 6 lake, RED 7 lake, Yellow 5 lake, Yellow 6 lake, Blue 1 lake.

Non-limiting examples of pigments useful in this composition are sold under name Unipure® pigments available from Sensient Cosmetic Technologies and titanate (ITT) treated pigments available from Kobo. Treated pigments are disclosed, for example, in U.S. Pat. Nos. 7,964,178, 5,108,736; 4,877,604; 9,328,244 as well as in US patent application publications Nos. US2018028025 and 2009185984, each of which is incorporated by reference in its entirety.

An amount of the at least one pigment in the composition may vary. For example, it may be from about 0.01 mass % to about 30.0 mass %, from about 0.1 mass % to about 28.0 mass or from about 0.5 mass % to about 26.0 mass % or from about 1.0 mass % to about 20.0 mass %.

In some embodiments, the composition may further comprise at least one powdery ingredient, which may comprise, for example, at least one texturizing powder. In some embodiments, the at least one powdery ingredient may comprise one or more of untreated silica powder; treated silica powder, such as hydrophobicaly treated silica powder, e.g. silica powder treated with silicone oils and/or silicone polymers and/or amino acids; mica.

An amount of the at least one powdery ingredient in the composition may vary. For example, it may be from about 0.1 mass % to about 30.0 mass %, from about 0.5 mass % to about 28.0 mass % or from about 1 mass % to about 20.0 mass % or from about 2.0 mass % to about 15 mass %.

In some embodiments, the composition may include at least one wax. In some embodiments, the at least one wax may include at least one wax, which is solid or semisolid at a room temperature of about 25 degrees C. Specific examples of waxes include, but are not limited to, natural and synthetic waxes, for example: a beeswax, a candelilla wax, a cotton wax, a carnauba wax, a bayberry wax, an insect wax, such as a wax secreted by *Ericerus pela*, spermaceti, a montan wax, a bran wax (rice wax), a capok wax, a Japan wax, lanolin acetate, liquid lanolin, sugar cane wax, esters of lanolin fatty acids and isopropyl alcohol, hexyl laurate, reduced lanolin, jojoba wax, hard lanolin, shellac wax, microcrystalline wax, paraffin wax, polyoxyethylene (POE) lanolin alcohol ethers, POE lanolin alcohol acetates, POE cholesterol ethers, esters of lanolin fatty acids and polyethylene wax, synthetic wax, fatty acid glycerides, hydrogenated castor oil, petrolatum, and POE hydrogenated lanolin alcohol ethers.

An amount of the at least one wax in the composition may vary. For example, in some embodiments, the amount of the at least one wax in the composition may be from about 5% to about 25%, from about 8% to about 20%, from about 10% to about 17% by mass relative to the total mass of the composition.

In some embodiments, the composition may include at least one solvent. In some embodiments, the at least one solvent may include a solvent having flash point below 50 degrees centigrade. In some embodiments, the at least one solvent may include a solvent having flash point above 70 degrees centigrade. In some embodiments, the at least one solvent may include at least one solvent selected from volatile and non-volatile hydrocarbons, volatile and non-volatile silicones, alcohols, glycols, esters, vegetable oils, and synthetic oils. In some embodiments, the at least one solvent may include at least one solvent which is selected from hydrocarbon solvents, such as hydrogenated polyisobutane, isododecane, or isohexadecane, and silicone based solvents, such as dimethicone, or simethicone.

An amount of the at least one solvent in the composition may vary. For example, the amount of the at least one solvent in the composition may be from about 10% to about 45% or from about 15% to about 42% or from about 20% to about 40% per by mass relative to the total mass of the composition.

In some embodiments, the composition may comprise at least one thickening agent. As used herein, "thickening agent" means an agent, contributing to modification of viscosity, thixotropic properties and stability of cosmetic compositions (e.g., reduces pigment sedimentation, syneresis). Thus, the at least one thickening agent may comprise, for example, at least one hydrophobic gelling agent and/or at least one hydrophilic gelling agent. In some embodiments, the at least one thickening agent may comprise a hydrocarbon thickening agent, a hydrophilic thickening agent, a hydrophobic thickening agent or any combination thereof.

In some embodiments, the composition may include at least one hydrophobic mineral gellant. In some embodiments, the at least one hydrophobic mineral gellant may include at least one gellant selected from organic modified clays and modified or unmodified hectorites and hydrophobic silicas, including fumed silicas. In some embodiments, the at least one hydrophobic mineral gellant may include at least one gellant selected from, for example, dimethyl distearyl ammonium hectorite, dimethyl distearyl ammonium bentonite, and dimethyl distearyl ammonium modified montmorillonite and others, as described and exemplified in U.S. Pat. Pub. No. 2007/0071703, which is hereby incorporated by reference in its entirety.

In some embodiments, the at least one hydrophobic mineral gellant may include at least gellant in which a quaternary ammonium salt compound is added to a natural or synthetic smectite clay mineral, such as bentonite, by way of an ion exchange reaction. The choice of organic modified clay minerals may be not particularly limited as long as it is cosmetically acceptable and may include, for example, dimethyl ammonium hectorite, benzyl dimethyl stearyl ammonium hectorite, and magnesium aluminum silicate treated with distearyl dimethyl ammonium chloride.

In some embodiments, the at least one hydrophobic mineral gellant may include at least one gellant selected, for example, from bentonites and organically modified hectorites pre-dispersed in organic solvents. A non-limiting example of commercially available bentonite is BENTONE GEL (Registered Trademark) series, including BENTONE GEL (Registered Trademark) ISD V (INCI: Isododecane, Disteardimonium Hectorite, Propylene Carbonate) available from Elementis Specialties. Another exemplary material is GARAMITE 7308XR (INCI: Quaternium-90 Sepiolite and Quaternium −90 Montmorillonite) available from Eckart.

In some embodiments, the suitable mineral gellant(s) may be utilized in a solid powder form or a gel, where the powder(s) are dispersed in a carrier, such as, for example, mineral oil, isohexadecane, isododecane, hydrogenated polyisobutane, C12-15 alkyl benzoate, and/or isonolnyl isononanoate.

In some embodiments, a thickening agent in the carrier may range from about 1.0% to about 20% or from about 2% to about 15% or from about 3% to about 12% by mass relative to the total mass of the composition.

In some embodiments, the cosmetic powder composition may also contain one or more additional optional ingredients, such as softening/conditioning agents, preservatives, emollients, film formers, surfactants, actives and combinations thereof.

In some embodiments, the composition may include at least one surfactant, such as a surfactant having an HLB value which equals or is less than 14, including nonionic surfactants having an HLB value from 2 to 14.

In some embodiments, the composition may include at least polyethylene glycol derivatives of dimethicone, such as PEG-8 to PEG-12 dimethicone surfactants and those described in U.S. Pat. No. 7,842,725. Suitable but non-limiting examples of polyethylene glycol derivatives of dimethicone may include PEG-12 dimethicone and PEG-10 dimethicone, both having HLB value of less than 14.

An amount of the one or more additional ingredients may vary. For example, in some embodiments, the additional optional ingredients may be present from about 0.01% to about 10%, from about 0.1% to about 8% or from 0.2% to 6% or from about 0.3% to about 5%.

Embodiments described herein are further illustrated by, though in no way limited to, the following working examples.

Example

A number of exemplary cosmetic compositions was prepared using ingredients summarized in Tables 1-8.

TABLE 1

Exemplary sunscreen composition.

| Phase | Ingredient/INCI name (Trade name) | Supplier | Mass % |
|---|---|---|---|
| A | ISOHEXADECANE (PERMETHYL 101 A) | PRESPERSE CORPORATION | 6.70 |
| A | ISODODECANE (PERMETHYL 99A) | PRESPERSE CORPORATION | 19.00 |
| A | DIMETHICONE (DM-FLUID-2CS (KF-96A-2CS)) | SHIN-ETSU SILICONES OF AMERICA | 7.00 |
| A | ISODODECANE, DISTEARDIMONIUM HECTORITE, PROPYLENE CARBONATE (BENTONE GEL ISD V #10932) | ELEMENTIS SPECIALTIES | 16.00 |
| A | POLYPHENYLSILSESQUIOXANE, TRIMETHYLSILOXYSILICATE, DIMETHICONE (GRANRESIN PHQ-C/FS) | GRANT INDUSTRIES | 12.00 (10.20 resin) |
| A | PEG/PPG-18/18 DIMETHICONE, DIMETHICONE (GRANSURF 50C-HM) | GRANT INDUSTRIES | 1.80 (0.91 active) |
| A | ETHYLHEXYLGLYCERIN (LEXGARD E) | NEXEO SOLUTIONS | 0.30 |
| A | SORBITAN SESQUIISOSTEARATE (ESTEMOL 182 V) | SHISEIDO COMPANY LTD. | 2.00 |
| A | POLYETHYLENE (PERFORMALENE ™ 400 (1%) and PERFORMALENE ™ PL(3%)) | UNIVAR USA INC. | 4.00 |
| A | CANDELILLA CERA, BENZYL ALCOHOL (CANDELILLA WAX SP-75) | STRAHL AND PITSCH, LLC. | 1.00 |

TABLE 1-continued

| Exemplary sunscreen composition. | | | |
|---|---|---|---|
| Phase | Ingredient/INCI name (Trade name) | Supplier | Mass % |
| A | JOJOBA ESTERS, HELIANTHUS ANNUUS SEED CERA, ACACIA DECURRENS FLOWER CERA, POLYGLYCERIN-3 (ACTICIRE MB 5909) | GATTEFOSSE USA | 2.00 |
| B | DIMETHICONE, CETEARYL DIMETHICONE CROSSPOLYMER (VELVESIL DM) | MOMENTIVE PERFORMANCE MATERIAL | 2.50 |
| B | MICA (MICA SILVER 2800) | AMERILURE INC. | 0.70 |
| B | BIS-PEG-18 METHYL ETHER DIMETHYL SILANE, BHT (Cosmetic Wax 2501) | SHISEIDO COMPANY LTD. | 2.00 |
| B | MICA, THEOBROMA CACAO SEED BUTTER, TOCOPHERYL ACETATE, QUERCETIN (BUTTERPOWDER MCB91-Q) | BLUE SUN INTERNATIONAL | 3.00 |
| C | ZINC OXIDE, COCO-CAPRYL ATE/CAPRATE, POLYGLYCERYL-3 POLYRICINOLEATE, ISOSTEARIC ACID (G-BLOCK DZ 370 CCT) | APPLECHEM, INC | 20.00 |
| | | | 100.00 |

TABLE 2

| Exemplary Mascara Composition | | | |
|---|---|---|---|
| Phase | Ingredient INCI name/Trade name | Supplier | Mass % |
| A | ISOHEXADECANE//PERMETHYL 101A | PRESPERSE CORPORATION | 7.75 |
| A | ISODODECANE/PERMETHYL 99A | PRESPERSE CORPORATION | 18.00 |
| A | DIMETHICONE/KF-96A-2CS | SHIN-ETSU SILICONES OF AMERICA | 5.00 |
| A | ISODODECANE, DISTEARDIMONIUM HECTORITE, PROPYLENE CARBONATE/ BENTONE GEL ISD V #10932 | ELEMENTIS SPECIALTIES | 16.00 |
| A | POLYPHENYLSILSESQUIOXANE, TRIMETHYLSILOXYSILICATE, DIMETHICONE/GRAN RESIN PHQ-CA | GRANT INDUSTRIES | 14.25 |
| A | PEG/PPG-18/18 DIMETHICONE, DIMETHICONE/GRANSURF 50C-HM | GRANT INDUSTRIES | 1.80 (0.91 active) |
| A | ETHYLHEXYLGLYCERIN/ LEXGARD E | NEXEO SOLUTIONS | 0.30 |
| A | SORBITAN SESQUIISOSTEARATE/ ESTEMOL 182 V | SHISEIDO COMPANY LTD. | 2.00 |
| A | POLYETHYLENE/PERFORMALENE 400 | UNIVAR USA INC. | 4.00 |
| A | POLYETHYLENE/PERFORMALENE PL | UNIVAR USA INC. | 6.65 |
| A | CANDELILLA CERA, BENZYL ALCOHOL/CANDELILLA WAX SP-75 | STRAHL AND PITSCH, LLC. | 2.50 |
| A | JOJOBA ESTERS, HELIANTHUS ANNUUS SEED CERA, ACACIA DECURRENS FLOWER CERA, POLYGLYCERIN-3/ACTICIRE MB 5909 | GATTEFOSSE USA | 2.00 |
| B | MICA/MICA SILVER 2800 | AMERILURE INC. | 0.20 |
| B | SILICA/SATINIER M5 | SHISEIDO COMPANY LTD. | 2.89 |
| B | MICA, THEOBROMA CACAO SEED BUTTER, TOCOPHERYL ACETATE, QUERCETIN/BUTTERPOWDER MCB91-Q | BLUE SUN INTERNATIONAL | 3.00 |
| B | MICA, SILICA, POLYURETHANE-15/ URETENDER V-640 | IKEDA CORPORATION OF AMERICA | 4.50 |
| B | DIMETHICONE, CETEARYL DIMETHICONE CROSSPOLYMER/VELVESIL DM | MOMENTIVE PERFORMANCE MATERIAL | 1.50 |

TABLE 2-continued

| Phase | Ingredient INCI name/Trade name | Supplier | Mass % |
|---|---|---|---|
| Exemplary Mascara Composition | | | |
| C | CI 77499, ISOPROPYL TITANIUM TRIISOSTEARATE, BIS-PEG-15 DIMETHICONE/IPDI COPOLYMER, PEG-2 SOYAMINE/UNIPURE BLACK-LC 989 ADT-C | SENSIENT COSMETIC TECHNOLOGIES GRANT INDUSTRIES | 7.66 |
| | | | 100.00 |

TABLE 3

| Phase | Ingredient INCI name/Trade name | Supplier | Mass % |
|---|---|---|---|
| Exemplary Eye Brow Composition | | | |
| A | ISOHEXADECANE/PERMETHYL 101A | PRESPERSE CORPORATION | 11.45 |
| A | ISODODECANE/PERMETHYL 99A | PRESPERSE CORPORATION | 19.70 |
| A | DIMETHICONE/KF-96A-2CS | SHIN-ETSU SILICONES OF AMERICA | 5.00 |
| A | ISODODECANE, DISTEARDIMONIUM HECTORITE, PROPYLENE CARBONATE/ BENTONE GEL ISD V#10932 | ELEMENTIS SPECIALTIES | 16.00 |
| A | POLYPHENYLSILSESQUIOXANE, TRIMETHYLSILOXYSILICATE, DIMETHICONE/GRAN RESIN PHQ-CA | GRANT INDUSTRIES | 14.25 |
| A | PEG/PPG-18/18 DIMETHICONE, DIMETHICONE/GRANSURF 50C-HM | GRANT INDUSTRIES | 1.80 (0.91 active) |
| A | ETHYLHEXYLGLYCERIN/LEXGARD E | NEXEO SOLUTIONS | 0.30 |
| A | SORBITAN SESQUIISOSTEARATE/ESTEMOL 182 V | SHISEIDO COMPANY LTD. | 2.00 |
| A | POLYETHYLENE/PERFORMALENE 400 | UNIVAR USA INC. | 4.00 |
| A | POLYETHYLENE/PERFORMALENE PL | UNIVAR USA INC. | 6.65 |
| A | CANDELILLA CERA, BENZYL ALCOHOL/CANDELILLA WAX SP-75 | STRAHL AND PITSCH, LLC. | 1.50 |
| A | JOJOBA ESTERS, HELIANTHUS ANNUUS SEED CERA, ACACIA DECURRENS FLOWER CERA, POLYGLYCERIN-3/ACTITIRE MB 5909 | GATTEFOSSE USA | 2.00 |
| B | DIMETHICONE, CETEARYL DIMETHICONE CROSSPOLYMER/VELVESIL DM | MOMENTIVE PERFORMANCE MATERIAL | 2.00 |
| B | MICA/MICA SILVER 2800 | AMERILURE INC. | 0.46 |
| B | SILICA/SATINIER M5 | SHISEIDO COMPANY LTD. | 2.89 |
| B | MICA, THEOBROMA CACAO SEED BUTTER, TOCOPHERYL ACETATE, QUERCETIN/BUTTERPOWDER MCB91-Q | BLUE SUN INTERNATIONAL | 3.00 |
| C | CI 77499, ISOPROPYL TITANIUM TRIISOSTEARATE, BIS-PEG-15 DIMETHICONE/IPDI COPOLYMER, PEG-2 SOYAMINE/UNIPURE BLACK LC 989 ADT-C | SENSIENT COSMETIC TECHNOLOGIES | 7.00 |
| | | | 100.00 |

TABLE 4

| Phase | Ingredient INCI name/Trade name | Supplier | Mass % |
|---|---|---|---|
| Exemplary Concealer Composition | | | |
| A | ISOHEXADECANE/PERMETHYL 101A | PRESPERSE CORPORATION | 10.25 |
| A | ISODODECANE/PERMETHYL 99A | PRESPERSE CORPORATION | 11.10 |

TABLE 4-continued

| Exemplary Concealer Composition | | | |
|---|---|---|---|
| Phase | Ingredient INCI name/Trade name | Supplier | Mass % |
| A | DIMETHICONE/KF-96A-2CS | SHIN-ETSU SILICONES OF AMERICA | 5.55 |
| A | POLYPHENYLSILSESQUIOXANE, TRIMETHYLSILOXYSILICATE, DIMETHICONE/GRAN RESIN PHQ-CA | GRANT INDUSTRIES | 11.50 |
| A | PEG/PPG-18/18 DIMETHICONE, DIMETHICONE/GRANSURF 50C-HM | GRANT INDUSTRIES | 0.11 (0.06 active) |
| A | ETHYLHEXYLGLYCERIN/ LEXGARD E | NEXEO SOLUTIONS | 0.30 |
| A | SORBITAN SESQUIISOSTEARATE/ ESTEMOL 182V | SHISEIDO COMPANY LTD. | 1.67 |
| A | ISODODECANE, DISTEARDIMONIUM HECTORITE, PROPYLENE CARBONATE/BENTONE GEL ISD V #10932 | ELEMENTIS SPECIALTIES | 16.25 |
| A | SIMETHICONE/TSA 750S | SHISEIDO COMPANY LTD. | 0.02 |
| A | TOCOPHEROL/E-MIX-D | SHISEIDO COMPANY LTD. | 0.15 |
| A | POLYETHYLENE/ PERFOMALENE PL | UNIVAR USA INC. | 7.77 |
| A | POLYETHYLENE/ PERFORMALENE 400 | UNIVAR USA INC. | 3.33 |
| A | JOJOBA ESTERS, HELIANTHUS ANNUUS SEED CERA, ACACIA DECURRENS FLOWER CERA, POLYGLYCERIN-3/ACTICIRE MB 5909 | GATTEFOSSE USA | 2.78 |
| A | CANDELILLA CERA, BENZYL ALCOHOL/CANDELILLA WAX SP-75 | STRAHL AND PITSCH, LLC. | 1.69 |
| B | DIMETHICONE, CETEARYL DIMETHICONE CROSSPOLYMER/VELVESIL DM | MOMENTIVE PERFORMANCE MATERIAL | 1.67 |
| B | MICA/MICA SILVER 2800 | AMERILURE INC. | 0.91 |
| B | SILICA/SATINIER M5 | IKEDA CORPORATION OF AMERICA | 1.55 |
| B | HDI/TRIMETHYLOL HEXYLLACTONE CROSSPOLYMER, SILICA/ PLASTIC POWDER D-400 | SHISEIDO COMPANY LTD. | 3.00 |
| B | CALCIUM STEARATE/CALCIUM STEARATE V | SHISEIDO COMPANY LTD. | 0.05 |
| C | CI 77891 ISOPROPYL TITANIUM TRIISOSTEARATE, BIS-PEG-15 DIMETHICONE/IPDI COPOLYMER, PEG-2 SOYAMINE/UNIPURE WHITE LC 987 ADT-C | SENSIENT COSMETIC TECHNOLOGIES | 14.71 |
| C | CI 77492 ISOPROPYL TITANIUM TRIISOSTEARATE, BIS-PEG-15 DIMETHICONE/IPDI COPOLYMER, PEG-2 SOYAMINE/UNIPURE YELLOW LC 182 ADT-C | SENSIENT COSMETIC TECHNOLOGIES | 4.13 |
| C | CI 77499 ISOPROPYL TITANIUM TRIISOSTEARATE, BIS-PEG-15 DIMETHICONE/IPDI COPOLYMER, PEG-2 SOYAMINE/UNIPURE BLACK LC 989 ADT-C | SENSIENT COSMETIC TECHNOLOGIES | 0.14 |
| C | CI 77491 ISOPROPYL TITANIUM TRIISOSTEARATE, BIS-PEG-15 DIMETHICONE/IPDI COPOLYMER, PEG-2 SOYAMINE/UNIPURE RED LC 381 ADT-C | SENSIENT COSMETIC TECHNOLOGIES | 1.37 |
| | | | 100.00 |

TABLE 5

| Exemplary foundation composition | | | |
|---|---|---|---|
| Phase | Ingredient INCI name/Trade name | Supplier | RM % |
| A | ISOHEXADECANE/ PERMETHYL 101A | PRESPERSE CORPORATION | 12.10 |
| A | ISODODECANE/PERMETHYL 99A | PRESPERSE CORPORATION | 11.10 |
| A | DIMETHICONE/KF-96A-2CS | SHIN-ETSU SILICONES OF AMERICA | 5.55 |
| A | POLYPHENYL-SILSESQUIOXANE, TRIMETHYL SILOXYSILICATE, DIMETHICONE/GRANRESIN PHQ-CA | GRANT INDUSTRIES | 16.94 |
| A | PEG/PPG-18/18 DIMETHICONE, DIMETHICONE/GRANSURF 50C-HM | GRANT INDUSTRIES | 0.11(0.06 active) |
| A | ETHYLHEXYLGLYCERIN/ LEXGARD E | NEXEO SOLUTIONS | 0.30 |
| A | SORBITAN SESQUIISOSTEARATE/ ESTEMOL 182 V | SHISEIDO COMPANY LTD. | 1.67 |
| A | ISODODECANE, DISTEARDIMONIUM HECTORITE, PROPYLENE CARBONATE/BENTONE GEL ISDV #10932 | ELEMENTIS SPECIALTIES | 16.25 |
| A | SIMETHICONE/TSA 750S | SHISEIDO COMPANY LTD. | 0.02 |
| A | TOCOPHEROL/E-MIX-D | SHISEIDO COMPANY LTD. | 0.15 |
| A* | POLYETHYLENE/ PERFOMALENE PL (MW 500) | UNIVAR USA INC. | 7.77 |
| A* | POLYETHYLENE/ PERFOMALENE 400 (MW 400) | UNIVAR USA INC. | 3.33 |
| A | JOJOBA ESTERS, HELIANTHUS ANNUUS SEED CERA, ACACIA DECURRENS FLOWER CERA, POLYGLYCERIN-3/ACTICIRE MB 5909 | GATTEFOSSE USA | 2.78 |
| A | CANDELILLA CERA, BENZYL ALCOHOL/CANDELILLA WAX SP-75 | STRAHL AND PITSCH, LLC. | 1.69 |
| B | DIMETHICONE, CETEARYL DIMETHICONE CROSSPOLYMER/VELVESIL DM | MOMENTIVE PERFORMANCE MATERIAL | 1.67 |
| B | MICA/MICA SILVER 2800 | AMERILURE INC. | 1.28 |
| B | SILICA/SATINIER M5 | IKEDA CORPORATION OF AMERICA | 1.55 |
| B | HDI/TRIMETHYLOL HEXYLLACTONE CROSSPOLYMER, SILICA/ PLASTIC POWDER D-400 | SHISEIDO COMPANY LTD. | 3.00 |
| B | CALCIUM STEARATE/ CALCIUM STEARATE V | SHISEIDO COMPANY LTD. | 0.05 |
| C | CI 77891 ISOPROPYL TITANIUM TRIISOSTEARATE, BIS-PEG-15 DIMETHICONE/IPDI COPOLYMER, PEG-2 SOYAMINE/UNIPURE WHITE LC 987 ADT-C | SENSIENT COSMETIC TECHNOLOGIES | 8.74 |
| C | CI 77492 ISOPROPYL TITANIUM TRIISOSTEARATE, BIS-PEG-15 DIMETHICONE/IPDI COPOLYMER, PEG-2 SOYAMINE/UNIPURE YELLOW LC 182 ADT-C | SENSIENT COSMETIC TECHNOLOGIES | 2.89 |
| C | CI 77499 ISOPROPYL TITANIUM TRIISOSTEARATE, BIS-PEG-15 DIMETHICONE/IPDI COPOLYMER, PEG-2 SOYAMINE/UNIPURE BLACK LC 989 ADT-C | SENSIENT COSMETIC TECHNOLOGIES | 0.10 |

TABLE 5-continued

| Exemplary foundation composition | | | |
|---|---|---|---|
| Phase | Ingredient INCI name/Trade name | Supplier | RM % |
| C | CI 77491 ISOPROPYL TITANIUM TRIISOSTEARATE, BIS-PEG-15 DIMETHICONE/IPDI COPOLYMER, PEG-2 SOYAMINE/UNIPURE RED LC 381 ADT-C | SENSIENT COSMETIC TECHNOLOGIES | 0.96 |
| | | | 100.00 |

A*—two different waxes with different molecular weight

TABLE 6

| Exemplary Blush Composition | | | |
|---|---|---|---|
| Phase | Ingredient INCI name/Trade name | Supplier | Mass % |
| A | ISOHEXADECANE/PERMETHYL 101 A | PRESPERSE CORPORATION | 7.75 |
| A | ISODODECANE/PERMETHYL 99A | PRESPERSE CORPORATION | 18.00 |
| A | DIMETHICONE/KF 96A-2CS | SHIN-ETSU SILICONES OF AMERICA | 5.00 |
| A | ISODODECANE, DISTEARDIMONIUM HECTORITE, PROPYLENE CARBONATE/ BENTONE GEL ISD V#10932 | ELEMENTIS SPECIALTIES | 14.25 |
| A | POLYPHENYLSILSESQUIOXANE, TRIMETHYLSILOXYSILICATE, DIMETHICONE/GRANRESIN PHQ-CA | GRANT INDUSTRIES | 16.94 |
| A | PEG/PPG-18/18 DIMETHICONE, DIMETHICONE/GRANSURF 50C-HM | GRANT INDUSTRIES | 1.80 (0.91 active) |
| A | ETHYLHEXYLGLYCERIN/LEXGARD E | NEXEO SOLUTIONS | 0.30 |
| A | SYNTHETIC WAX/PERFORMA V825 POLYMER (RM-2542) | SHISEIDO COMPANY LTD. | 2.00 |
| A | POLYETHYLENE/PERFORMALENE 400 | UNIVAR USA INC. | 4.00 |
| A | POLYETHYLENE/PERFORMALENE PL | UNIVAR USA INC. | 6.65 |
| A | CANDELILLA CERA, BENZYL ALCOHOL/ CANDELILLA WAX SP-75 | STRAHL AND PITSCH, LLC. | 2.50 |
| A | JOJOBA ESTERS, HELIANTHUS ANNUUS SEED CERA, ACACIA DECURRENS FLOWER CERA, POLYGLYCERIN-3/ACTICIRE MB 5909 | GATTEFOSSE USA | 2.00 |
| B | MICA/MICA SILVER 2800 | AMERILURE INC. | 0.20 |
| B | SILICA/SATINIER M5 | SHISEIDO COMPANY LTD. | 2.89 |
| B | MICA, THEOBROMA CACAO SEED BUTTER, TOCOPHERYL ACETATE, QUERCETIN/ BUTTERPOWDER MCB91-Q | BLUE SUN INTERNATIONAL | 3.00 |
| B | MICA, SILICA, POLYURETHANE-15/ URETENDER V-640 | IKEDA CORPORATION OF AMERICA | 4.50 |
| B | DIMETHICONE, CETEARYL DIMETHICONE CROSSPOLYMER/VELVESIL DM | MOMENTIVE PERFORMANCE MATERIAL | 1.50 |
| C | CI 77499, ISOPROPYL TITANIUM TRIISOSTEARATE, BIS-PEG-15 DIMETHICONE/IPDI COPOLYMER, PEG-2 SOYAMINE/UNIPURE BLACK LC 989 ADT-C | SENSIENT COSMETIC TECHNOLOGIES | 7.66 |
| | | | 100.00 |

TABLE 7

| Exemplary lipstick composition. | | | |
|---|---|---|---|
| Phase | Ingredient | Supplier | Mass % |
| A | ISOHEXADECANE/PERMETHYL 101A | PRESPERSE CORPORATION | 12.395 |

TABLE 7-continued

Exemplary lipstick composition.

| Phase | Ingredient | Supplier | Mass % |
|---|---|---|---|
| A | ISODODECANE/PERMETHYL 99A | PRESPERSE CORPORATION | 10.00 |
| A | DIMETHICONE/KF-96A-2CS | SHIN-ETSU SILICONES OF AMERICA | 5.00 |
| A | POLYPHENYLSILSESQUIOXANE, TRIMETHYL SILOXYSILICATE, DIMETHICONE/GRANRESIN PHQ-CA | GRANT INDUSTRIES | 20.205 |
| A | PEG/PPG-18/18 DIMETHICONE, DIMETHICONE/GRANSURF 50C-HM | GRANT INDUSTRIES | 1.00 (0.51 active) |
| A | ETHYLHEXYLGLYCERIN/LEXGARD E | NEXEO SOLUTIONS | 0.30 |
| A | SORBITAN SESQUIISOSTEARATE/ ESTEMOL 182 V | SHISEIDO COMPANY LTD. | 1.50 |
| A | ISODODECANE, DISTEARDIMONIUM HECTORITE, PROPYLENE CARBONATE/BENTONE GEL ISD V#10932 | ELEMENTIS SPECIALTIES | 14.64 |
| A | SIMETHICONE/TSA 750S | SHISEIDO COMPANY LTD. | 0.02 |
| A | TOCOPHEROL/E-MIX-D | SHISEIDO COMPANY LTD. | 0.15 |
| B | DIMETHICONE, CETEARYL DIMETHICONE CROSSPOLYMER. VELVESIL DM | MOMENTIVE PERFORMANCE MATERIAL | 1.50 |
| A | POLYETHYLENE/PERFORMALENE PL | UNIVAR USA INC. | 7.00 |
| A | POLYETHYLENE/PERFORMALENE 400 | UNIVAR USA INC. | 3.00 |
| A | JOJOBA ESTERS, HELIANTHUS ANNUUS SEED CERA, ACACIA DECURRENS FLOWER CERA, POLYGLYCERIN-3/ACTICIRE MB5909 | GATTEFOSSE USA | 2.50 |
| A | CANDELILLA CERA, BENZYL ALCOHOL/CANDELILLA WAX SP-75 | STRAHL AND PITSCH, LLC. | 1.52 |
| B | MICA/MICA SILVER 2800 | AMERILURE INC. | 0.12 |
| B | SILICA/SATINIER M5 | IKEDA CORPORATION OF AMERICA | 1.40 |
| B | HDI/TRIMETHYLOL HEXYLLACTONE CROSSPOLYMER, SILICA/PLASTIC POWDER D-400 | SHISEIDO COMPANY LTD. | 2.70 |
| B | CALCIUM STEARATE/CALCIUM STEARATE V | SHISEIDO COMPANY LTD. | 0.05 |
| C | ALUMINUM HYDROXIDE, CI 15850, ISOPROPYL TITANIUM TRIISOSTEARATE, BIS-PEG-15 DIMETHICONE/IPDI COPOLYMER, PEG-2 SOYAMINE/UNIPURE CI 15850 | SENSIENT COSMETIC TECHNOLOGIES | 15.00 |
| | | | 100.00 |

The exemplary compositions of Tables 1-7 were prepared as follows. All compounds of phase A were heated in a sealed main container at 85-90° C. and mixed with lighting mixer (IKA RW20) at 250-2500 RPM until uniform. Compounds of phase B (if applicable) were added to the main container and mixed at 80-85° C. The mixing continued until all compounds are well dispersed. Compounds of phase C (if applicable) were added to the main container at 80-83 C. The mixing continued until a uniform composition was obtained. The finished compositions may be poured to an appropriate container(s) at 80-83 C.

TABLE 8

Exemplary lipstick composition containing a low amount of water.

| Phase | Ingredient INCI name/Trade Name* | Supplier | RM % |
|---|---|---|---|
| A | HYDROGENATED POLYISOBUTENE, TOCOPHEROL | ROSSOW USA INC | 14.95 |
| A | SYNTHETIC WAX | UNIVAR USA INC. | 4.50 |
| A | HYDROGENATED POLYISOBUTENE, ETHYLENE/PROPYLENE/ STYRENE COPOLYMER, BUTYLENE/ETHYLENE/ STYRENE COPOLYMER, BHT | CALUMET PENRECO, LLC | 7.00 |

TABLE 8-continued

Exemplary lipstick composition containing a low amount of water.

| Phase | Ingredient INCI name/Trade Name* | Supplier | RM % |
|---|---|---|---|
| B | ISODODECANE, DISTEARDIMONIUM HECTORITE, PROPYLENE CARBONATE | ELEMENTIS SPECIALTIES | 3.00 |
| C | JOJOBA ESTERS, HELIANTHUS ANNUUS SEED CERA, ACACIA DECURRENS FLOWER CERA, POLYGLYCERIN-3 | GATTEFOSSE USA | 4.00 |
| C | POLYETHYLENE | UNIVAR USA INC. | 14.11 |
| D | C9-12 ALKANE, COCO-CAPRYLATE/CAPRATE | GRANT INDUSTRIES | 11.04 |
| D | PEG-12 DIMETHICONE, TOCOPHEROL | UNIVAR USA INC. | 1.00 |
| D | PEG-10 DIMETHICONE, TOCOPHEROL | SHIN-ETSU SILICONES OF AMERICA | 0.50 |
| D | PEG/PPG-18/18 DIMETHICONE, DIMETHICONE | GRANT INDUSTRIES | 0.75 (0.38 active) |
| D | ISODODECANE | PRESPERSE CORPORATION | 4.00 |
| E | SILICA | IKEDA CORPORATION OF AMERICA | 2.00 |
| E | HDI/TRIMETHYLOL HEXYLLACTONE CROSSPOLYMER, SILICA | SHISEIDO COMPANY LTD. | 2.00 |
| E | LAUROYL LYSINE | AJINOMOTO NORTH AMERICA INC | 3.00 |
| E | MICA, SILICA | IKEDA CORPORATION OF AMERICA | 1.88 |
| E | SIMETHICONE | SHISEIDO COMPANY LTD. | 0.02 |
| F | AQUA | SUPPLIER NOT SPECIFIED | 10.00 |
| F | GLYCERIN | BRENNTAG NORTHEAST 2 | 0.25 |
| F | AGAR | SHISEIDO COMPANY LTD. | 0.25 |
| F | PHENOXYETHANOL | CLARIANT CORPORATION | 0.50 |
| G | ALUMINUM HYDROXIDE, POLYPHENYL-SILSESQUIOXANE, TRIMETHYL SILOXY-SILICATE, CI 15850, ISOHEXADECANE, DIMETHICONE, ISOPROPYL TITANIUM TRIISOSTEARATE, BIS-PEG-15 DIMETHICONE/IPDI COPOLYMER, PEG-2 SOYAMINE | | 15.05 (5.75 resin) |
| H | SYNTHETIC WAX | UNIVAR USA INC. | 0.20 |
| | | | 100.00 |

*Trade Names for ingredients of this formulation are the same trade names as in the previous examples.

All ingredients of phase A were added to a main container covered well and heated to 90-95 C. the batch was homogenized at 1400 RPM (using Primix homogenizer) for 5 minutes or until gel was completely dispersed and uniform. Then phase B was added and homogenization was continued until the mixture was uniform. Next, the homogenization was continued with adding ingredients of phase C. Both steps were conducted at 90-95 C. Then the temperature was lowered to 80-85 C and ingredients of phases D and E were added and homogenized. In a separate container, combined all ingredients of phase F, heated to 80-85 C with prop mixing while keeping batch covered to avoid water loss. Next, both mixtures were combined and mixed slowly at 83-85 C and homogenized for a minimum of 5 minutes at 1400-1700 RPM. At the end, ingredients of phases G and H were added until all ingredients were well dispersed.

TABLE 9

| | A Composition of table 8 (silicone resin and emulsifier) | B Control Composition 1 (silicone resin, no emulsifier ) | C Control Composition 2 (water based, does not contain silicone resin) |
|---|---|---|---|
| SOFT MELTING SENSATION | 3 | 1 | 3 |
| VIBRANT | 3 | 2 | 3 |
| GLIDE | 3 | 2 | 1 |
| EVEN APPLICATION | 3 | 2 | 3 |
| LIGHT WEIGHT | 3 | 2 | 3 |
| DOES NOT FEEL TIGHT ON LIPS | 3 | 3 | 3 |

TABLE 9-continued

| | A Composition of table 8 (silicone resin and emulsifier) | B Control Composition 1 (silicone resin, no emulsifier ) | C Control Composition 2 (water based, does not contain silicone resin) |
|---|---|---|---|
| NON STICKY | 3 | 3 | 1 |
| COMFORTABLE TO WEAR ALL DAY | 3 | 2 | 3 |
| DOES NOT FLAKE OR PEEL | 3 | 1 | 3 |
| LIPS DOES NOT FEEL DRY AFTER WEAR | 3 | 3 | 2 |
| COLOR DOES NOT FADE | 3 | 2 | 3 |
| WEAR | 3 | 2 | 2 |

Method of evaluation of the compositions in Table 9 was as follows:

Five (5) independent panelists, which were typical lipstick users, ranging in age from 22-60, tested each of the compositions on separate days. The panelists were asked to apply the products only once and wear it for 8-12 hours without any restrictions (eating and drinking was allowed). Re-applications of tested products was not permitted. At the end of the wearing time, the products were evaluated for the characteristics listed in Table 9. All parameters were rated using the grading scale from 1 to 3, as described below:

3: Very good: The panelists reported lipsticks having all characteristics as listed hereinabove.

2: Acceptable: The panelists reported lipsticks having only some of the characteristics listed hereinabove.

1: Not acceptable: The panelists reported lipsticks having none of the characteristics listed hereinabove.

TABLE 10

Control Composition 1 (no PEG based emulsifier) from Table 9

| Phase | Ingredient INCI name* | Supplier | Mass % |
|---|---|---|---|
| A | ISOHEXADECANE | PRESPERSE CORPORATION | 13.395 |
| A | ISODODECANE | PRESPERSE CORPORATION | 10.00 |
| A | DIMETHICONE | SHIN-ETSU SILICONES OF AMERICA | 5.00 |
| A | POLYPHENYLSILSESQUIOXANE, TRIMETHYLSILOXYSILICATE, DIMETHICONE | GRANT INDUSTRIES | 20.205 |
| A | ETHYLHEXYLGLYCERIN | NEXEO SOLUTIONS | 0.30 |
| A | SORBITAN SESQUIISOSTEARATE | SHISEIDO COMPANY LTD. | 1.50 |
| A | ISODODECANE, DISTEARDIMONIUM HECTORITE, PROPYLENE CARBONATE | ELEMENTIS SPECIALTIES | 14.64 |
| A | SIMETHICONE | SHISEIDO COMPANY LTD. | 0.02 |
| A | TOCOPHEROL | SHISEIDO COMPANY LTD. | 0.15 |
| A | POLYETHYLENE | UNIVAR USA INC. | 7.00 |
| A | POLYETHYLENE | UNIVAR USA INC. | 3.00 |
| A | JOJOBA ESTERS, HELIANTHUS ANNUUS SEED CERA, ACACIA DECURRENS FLOWER CERA, POLYGLYCERIN-3 | GATTEFOSSE USA | 2.50 |
| A | CANDELILLA CERA, BENZYL ALCOHOL | STRAHL AND PITSCH, LLC. | 1.52 |
| B | DIMETHICONE, CETEARYL DIMETHICONE CROSSPOLYMER | MOMENTIVE PERFORMANCE MATERIAL | 1.50 |
| B | MICA | AMERILURE INC. | 0.12 |
| B | SILICA | IKEDA CORPORATION OF AMERICA | 1.40 |
| B | HDI/TRIMETHYLOL HEXYLLACTONE CROSSPOLYMER, SILICA | SHISEIDO COMPANY LTD. | 2.70 |
| B | CALCIUM STEARATE | SHISEIDO COMPANY LTD. | 0.05 |
| C | ALUMINUM HYDROXIDE, CI 15850, ISOPROPYL TITANIUM TRIISOSTEARATE, BIS-PEG-15 DIMETHICONE/IPDI COPOLYMER, PEG-2 SOYAMINE | SENSIENT COSMETIC TECHNOLOGIES | 15.00 |
| | | | 100.00 |

*Trade Names for ingredients of this formulation are the same trade names as in the previous examples.

Control Composition 2: hydrogenated polyisobutene, water, synthetic wax, polyethylene, isododecane, C9-12 alkane, lauroyl lysine, jojoba esters, silica, HDI/trimethylol hexyllactone crosspolymer, mica, *Helianthus annuus* (sunflower) seed cera, ethylene/propylene/styrene copolymer, PEG-12 dimethicone, PEG-10 dimethicone, coco-caprylate/caprate, disteardimonium hectorite, glycerin, agar agar, propylene carbonate, isopropyl titanium triisostearate, *Acacia decurrens* flower wax, polyglycerin-3, butylene/ethylene/styrene copolymer, organic silicon resin, butylated hydroxytoluene, vitamin E, phenoxyethanol, pigments.

The test results demonstrate that in terms of softness and melting sensation, the composition of Table 8 is comparable with Control Composition 2, which does not contain silicone resin or other film forming polymers. In terms of the wear results, the composition of Table 8 outperforms both Control Composition 1 and Control Composition 2. For the other tested categories, the composition of Table 8 performed better or at least was comparable with the control compositions.

TABLE 11

Exemplary Foundation Composition with SPF (Sun Protection Factor)

| Phase | EU INCI/Trade Name* | Supplier | RM % |
|---|---|---|---|
| A | ISOHEXADECANE | PRESPERSE CORPORATION | 1.03 |
| A | ISODODECANE | PRESPERSE CORPORATION | 4.00 |
| A | DIMETHICONE | SHIN-ETSU SILICONES OF AMERICA | 8.00 |
| A | POLYPHENYLSILSEQUIOXANE, TRIMETHYL SILOXYSILICATE, DIMETHICONE | GRANT INDUSTRIES | 3.50 |
| A** | POLYGLYCERYL-6 POLYHYDROXYSTEARATE (1.387%), POLYGLYCERYL-6 POLYRICINOLEATE (1.387%), POLYGLYCERIN-6 (0.225%), TOCOPHEROL, ASCORBYL PALMITATE/Trade name: Emulium Illustro | GATTEFOSSE USA | 3.00 |
| A** | POLYGLYCERYL-3 DIISOSTEARATE/Trade name: Plurol DiisosteariQue CG | GATTEFOSSE USA | 2.50 |
| A | SIMETHICONE | SHISEIDO COMPANY LTD. | 0.10 |
| A | CAPRYLIC/CAPRIC TRIGLYCERIDE, SALICORNIA HERBACEA EXTRACT | BARNET | 0.40 |
| A | SORBITAN SESQUIISOSTEARATE | SHISEIDO COMPANY LTD. | 2.50 |
| A | ISODODECANE, DISTEARDIMONIUM HECTORITE, PROPYLENE CARBONATE | ELEMENTIS SPECIALTIES | 14.00 |
| A | DIMETHICONE, CETEARYL DIMETHICONE CROSSPOLYMER | SHISEIDO COMPANY LTD. | 6.00 |
| A | JOJOBA ESTERS, HELIANTHUS ANNUUS SEED CERA, ACACIA DECURRENS FLOWER CERA, POLYGLYCERIN-3 | GATTEFOSSE USA | 4.00 |
| A | CANDELILLA CERA, BENZYL ALCOHOL | STRAHL AND PITSCH, LLC. | 1.20 |
| B | ZINC OXIDE, CAPRYLIC/CAPRIC TRIGLYCERIDE, POLYHYDROXYSTEARIC ACID, POLYGLYCERYL-3 POLYRICNOLEATE, ISOSTEARIC ACID, LECITHIN | APPLECHEM | 20.00 |
| B | ETHYLHEXYLGLYCERIN | NEXEO SOLUTIONS | 0.30 |
| B | TOCOPHEROL | SHISEIDO COMPANY LTD. | 0.02 |
| B | MICA | AMERILURE INC. | 3.00 |
| B | MICA, THEOBROMA CACAO(COCOA)SEED BUTTERS, TOCOPHERYL ACETATE, QUERCETIN | BLUE SUN | 6.40 |
| B | CALCIUM STEARATE | SHISEIDO COMPANY LTD. | 0.05 |
| C | CI 77492, CI 77499, CI 77491, CI 77891, ISOPROPYL TITANIUM TRIISOSTEARATE, BIS-PEG-15 DIMETHICONE/IPDI COPOLYMER, PEG-2 SOYAMINE | SENSIENT COSMETIC TECHNOLOGIES | 20.00 |
| | | | 100.00 |

*Trade Names for ingredients of this formulation are the same as the trade names in the previous examples with exemption of the ingredients under A**.

For preparing the composition of Table 11, all compounds of phase A were heated in a sealed main container at 85-90° C. and mixed with a lighting mixer (IKA RW20) at 250-2500 RPM until uniform. Compounds of phase B were added to the main container and mixed at 80-85° C. The mixing continued until all compounds are well dispersed. Compounds of phase C were added to the main container at 80-83C. The mixing continued with high sheer until a uniform composition was obtained. Drop batch at 30-25° C. The finished composition may be poured into an appropriate container(s) at 30-25° C. Unlike the compositions of Tables 1-8, the composition of Table 11 uses polyglyceryl emulsifier(s) instead of silicone emulsifier(s).

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

What is claimed is:

1. A cosmetic composition comprising:

0.01 mass % to 40 mass % of a silicone resin composition consisting of polyphenylsilsesquioxane/trimethylsiloxysilicate copolymer and dimethicone;

0.01 mass % to 5 mass of PEG/PPG-18/18 dimethicone, 10 mass % to 45 mass % of a solvent selected from the group consisting of hydrocarbon solvents and silicone based solvents;

1.0 mass % to about 20 mass % of Disteardimonium Hectorite;

10 mass % or less of water; and 0.01 mass % to about 10 mass % of at least one additional ingredient selected from the group consisting of softening/conditioning agents, preservatives, emollients, film formers, surfactants, actives and combinations thereof, wherein said silicone resin composition is the only silicone resin composition in the cosmetic composition, wherein the at least one additional ingredient comprises PEG-12 dimethicone and PEG-10 dimethicone, and wherein the PEG/PPG-18/18 dimethicone, the PEG-12 dimethicone and the PEG-10 dimethicone are the only surfactants in the composition.

2. The cosmetic composition of claim 1, comprising 2.0 mass % to 20 mass % of the silicone resin composition.

3. The cosmetic composition of claim 1, comprising 0.5 mass % to 3.5 mass % of PEG/PPG-18/18 dimethicone.

4. The cosmetic composition of claim 1, comprising 2 mass % to about 15 mass % of Disteardimonium Hectorite.

5. The cosmetic composition of claim 1, comprising 20 mass % to 40 mass % of the solvent.

6. The cosmetic composition of claim 1, comprising:

2.0 mass % to 20 mass % of the silicone resin composition;

0.5 mass % to 3.5 mass % of PEG/PPG-18/18 dimethicone;

2 mass % to about 15 mass % of Disteardimonium Hectorite; and 20 mass % to 40 mass % of the solvent.

7. The cosmetic composition of claim 6, wherein the cosmetic composition is a lipstick composition.

8. The cosmetic composition of claim 1, wherein the cosmetic composition is a lipstick composition.

9. The cosmetic composition of claim 1, further comprising from about 5 mass % to about 25 mass % of at least one wax.

10. The cosmetic composition of claim 6, further comprising from about 5 mass % to about 25 mass % of at least one wax.

11. The cosmetic composition of claim 1, further comprising from 0.01 mass % to 30 mass % of at least one pigment.

12. A method comprising applying the cosmetic composition of claim 1 to a keratinous surface.

* * * * *